US008207279B2

(12) United States Patent
Choi et al.

(10) Patent No.: US 8,207,279 B2
(45) Date of Patent: Jun. 26, 2012

(54) METHOD FOR PREPARING NORBORNENE MONOMER COMPOSITION, NORBORNENE POLYMER PREPARED THEREFROM, OPTICAL FILM COMPRISING THE NORBORNENE POLYMER, AND METHOD FOR PREPARING THE NORBORNENE POLYMER

(75) Inventors: Dai-Seung Choi, Daejeon (KR); Hye-Young Jung, Daejeon (KR); Sung-Don Hong, Daejeon (KR); Jung-Min Lee, Daejeon (KR); Hee-Jean Lee, Daejeon (KR); Sung-Ho Chun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 369 days.

(21) Appl. No.: 12/308,853

(22) PCT Filed: Jun. 26, 2007

(86) PCT No.: PCT/KR2007/003104
§ 371 (c)(1),
(2), (4) Date: Dec. 24, 2008

(87) PCT Pub. No.: WO2008/002066
PCT Pub. Date: Jan. 3, 2008

(65) Prior Publication Data
US 2010/0010177 A1    Jan. 14, 2010

(30) Foreign Application Priority Data
Jun. 26, 2006   (KR) .................. 10-2006-0057627

(51) Int. Cl.
*C08F 2/00* (2006.01)
*C07C 67/00* (2006.01)
*C08F 236/20* (2006.01)

(52) U.S. Cl. .......... 526/75; 526/172; 526/281; 560/241; 560/256; 560/261

(58) Field of Classification Search .............. 526/75, 526/172, 281, 282; 560/241, 256, 261; 349/118
See application file for complete search history.

(56) References Cited

U.S. PATENT DOCUMENTS

| | | | |
|---|---|---|---|
| 3,330,815 A | | 7/1967 | McKeon et al. |
| 3,705,136 A | * | 12/1972 | McGusty et al. ............. 526/282 |
| 5,962,703 A | | 10/1999 | Moszner et al. |
| 6,538,087 B2 | | 3/2003 | Zhao et al. |
| 6,875,555 B1 | | 4/2005 | Feiring et al. |
| 7,989,571 B2 | | 8/2011 | Chun et al. |
| 2002/0128408 A1 | | 9/2002 | Goodall et al. |
| 2004/0063982 A1 | | 4/2004 | Takahashi et al. |
| 2004/0254318 A1 | * | 12/2004 | Chun et al. .................. 526/171 |
| 2005/0010006 A1 | * | 1/2005 | Chun et al. .................. 526/171 |
| 2005/0186502 A1 | | 8/2005 | Elce et al. |

FOREIGN PATENT DOCUMENTS
SU   1368310   *   1/1988

OTHER PUBLICATIONS

Hawley's Condensed Chemical Dictionary, 14th Ed., 2002, Entry for Irganox.*
English language translation of SU 1368310; publication date: Jan. 1988.*
Transition-metal-catalyzed vinyl addition polymerizations of norbornene dericatives with ester groups; S Breunig, et al.; Makromol, Chem 193. 2915-2927 (1992).
($N^3$-Allyl) palladium (II) and Palladium (II) Nitrile Catalysts for the Addition Polymerization of Norbornene Derivatives with Functional Groups; Matthew et al.; Macromolecules 1996, 29, 2755-2763.
Addition Polymerization of Functionalized Norbornenes: The Effect of Size, Sterochemistry, and Coordinating Ability of the Substituent; Funk et al.; Organometallics 2004, 23, 1680-1683.
Novel, Efficient, Palladium-Based System for the Polymerization of Norbornene Derivatives: Scope and Mechanism; Hennis et al.; Organometallics 2001-20, 2802-2812.
Mechanistic Aspects of Metal-Catalyzed Alternating Copolymerization of Olefins with Carbon Monoxide; Sen; Acc Chem. Res. 1993, 26, 303-310.
Stereochemistry of the Diels-Alder Reaction; Martin, et al.; Department of Chemistry , Davidson College, Davidson, North Carolina and Department of Chemistry, Princeton University, Princeton, New Jersey Jan. 1961.
Ring-Opening Polymerization of Cyclic Olefins Substituted with Polar Groups. 5 Norbornene-2,3-Dicarbozy Anhydride (CPD.MA) Castner, et al. ; Journal of Molecular Catalysis, 15 (1982) 47-59. The Reaction of Norbornylene with N-Bromosuccinimide. Notricyclene and its Derivatives; Roberts, et al. ; Department of Chemistry and Laboratory of Nuclear Science and Engineering Massachusetts Institute of Technology Oct. 1949.
Formation of Nortricyclene Derivatives by Bromination of exo-2,5-Methylene-1,2,5,6-tetrahydrobenzoic Acids; Nooy, et al; Department of Chemistry, University of Michigan Jul. 1955.
Fine-Tuned Remote Control of Electrophilic Additions to Substituted Norbornenes; Arjona, et al. J. Org. Chem. 1991, 56, 6227-6229.
An Improved Procedure for the Preparation of exo-Dicyclopentadiene; Nelson, et al.; Department of Chemistry, Saint Joseph's College, Philadelphia, PA Feb. 1975.
Addition of Acetic Acid to Bicyclo[22.21] Hepta-2,5-Diene Catalyzed by Platinum Complexes; Magoon et al.; Journal of Organometallic Chemistry, 55 (1973) 409-418.

(Continued)

*Primary Examiner* — Fred M Teskin
(74) *Attorney, Agent, or Firm* — McKenna Long & Aldridge LLP

(57) ABSTRACT

Disclosed is a method for producing a norbornene monomer composition, a norbornene polymer produced using the norbornene monomer composition, an optical film including the norbornene polymer, and a method for producing the norbornene polymer. The method includes reacting a reaction solution that contains cyclopentadiene, dicyclopentadiene, or a mixture of cyclopentadiene and dicyclopentadiene, an acetate compound, and a solvent so that a content of an exo isomer is 50 mol % or more. Variables such as a reaction temperature, a reaction time, a molar ratio between reactants, and addition of a solvent are controlled so that the exo isomer is contained in content of 50 mol % or more. Accordingly, it is possible to industrially produce an acetate norbornene addition polymer by using the acetate norbornene monomer composition containing the exo isomer in content of 50 mol % or more.

11 Claims, 5 Drawing Sheets

OTHER PUBLICATIONS

Lewis acid Catalysis of Diels-Alder Reaction in Water, Otto, et al.; J. Am. Chem. Soc. 1996, 118, 7702-7707.

Accurate and Simple Analytic Representation of the Electron-Gas Correlation Energy; Perdew, et al. Physical Review B vol. 45, No. 23; Jun. 1992.

A Multicenter Numerical Integration Scheme for Polyatomic Molecules; Becke; J. Che m. Phys. 88 (4), Feb. 1988.

An All-Electron Numerical Method for Solving the Local Density Functional for Polyatomic Molecules; Delley; J Chem Phys. 92 (1), Jan. 1990.

Analytic Energy Derivatives in the Numerical Local-Density -Functional Approach; Delley; J Chem Phys 94 (11) Jun. 1991.

From Molecules to Solids with the $DM_o l^3$ Approach; Delley; J Chem Phys 2000 vol. 113 No. 18.

* cited by examiner

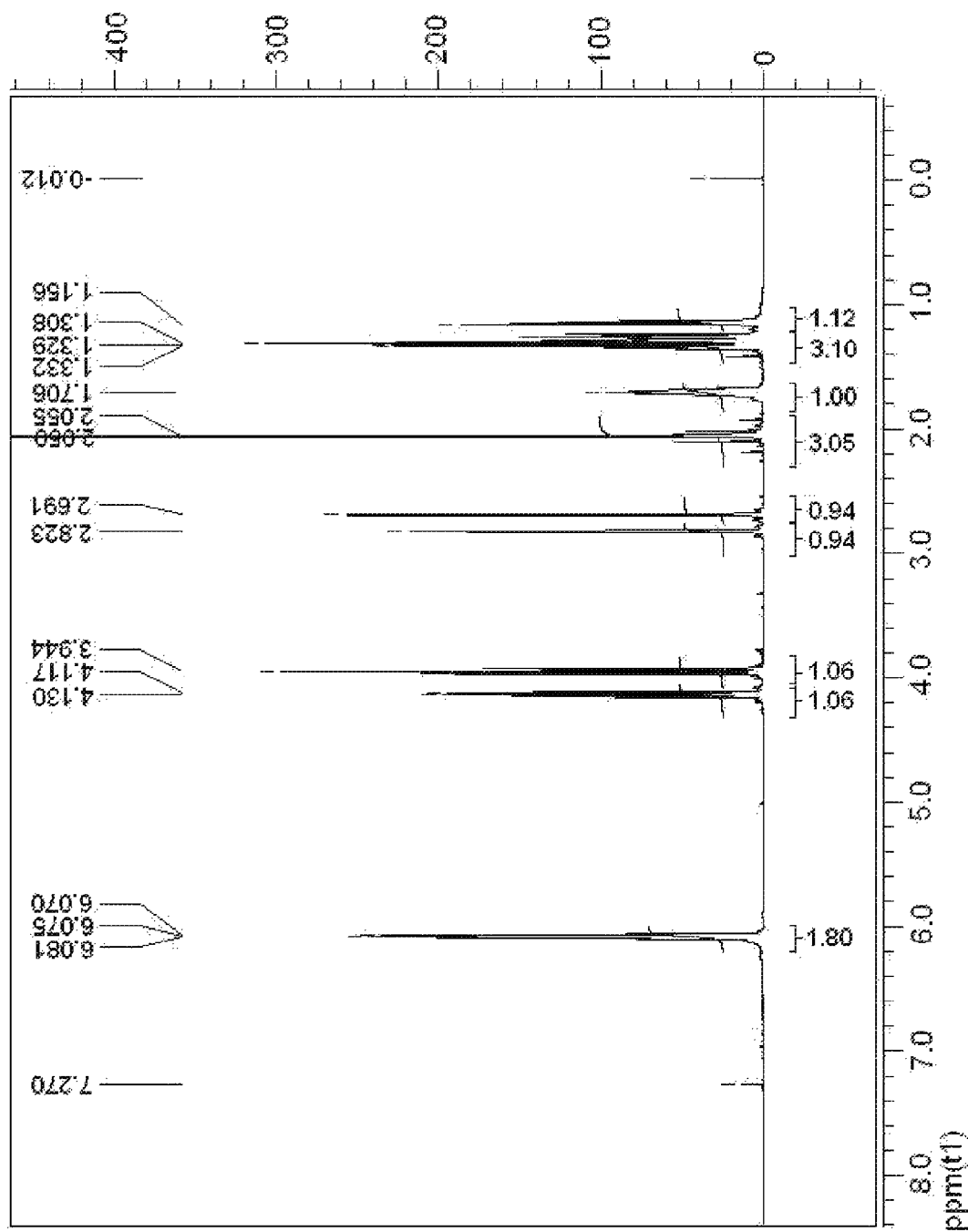
[Figure 1]

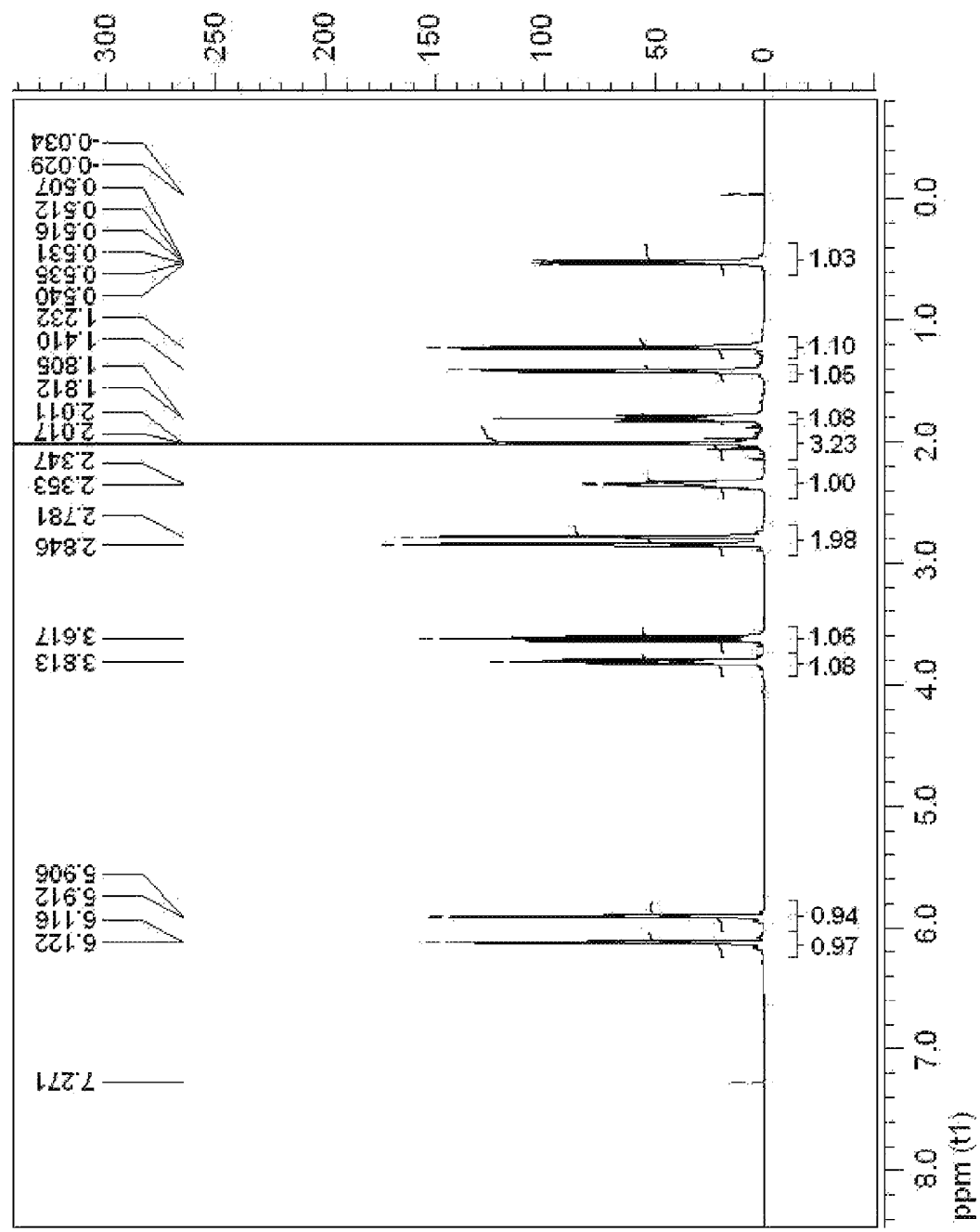
[Figure 2]

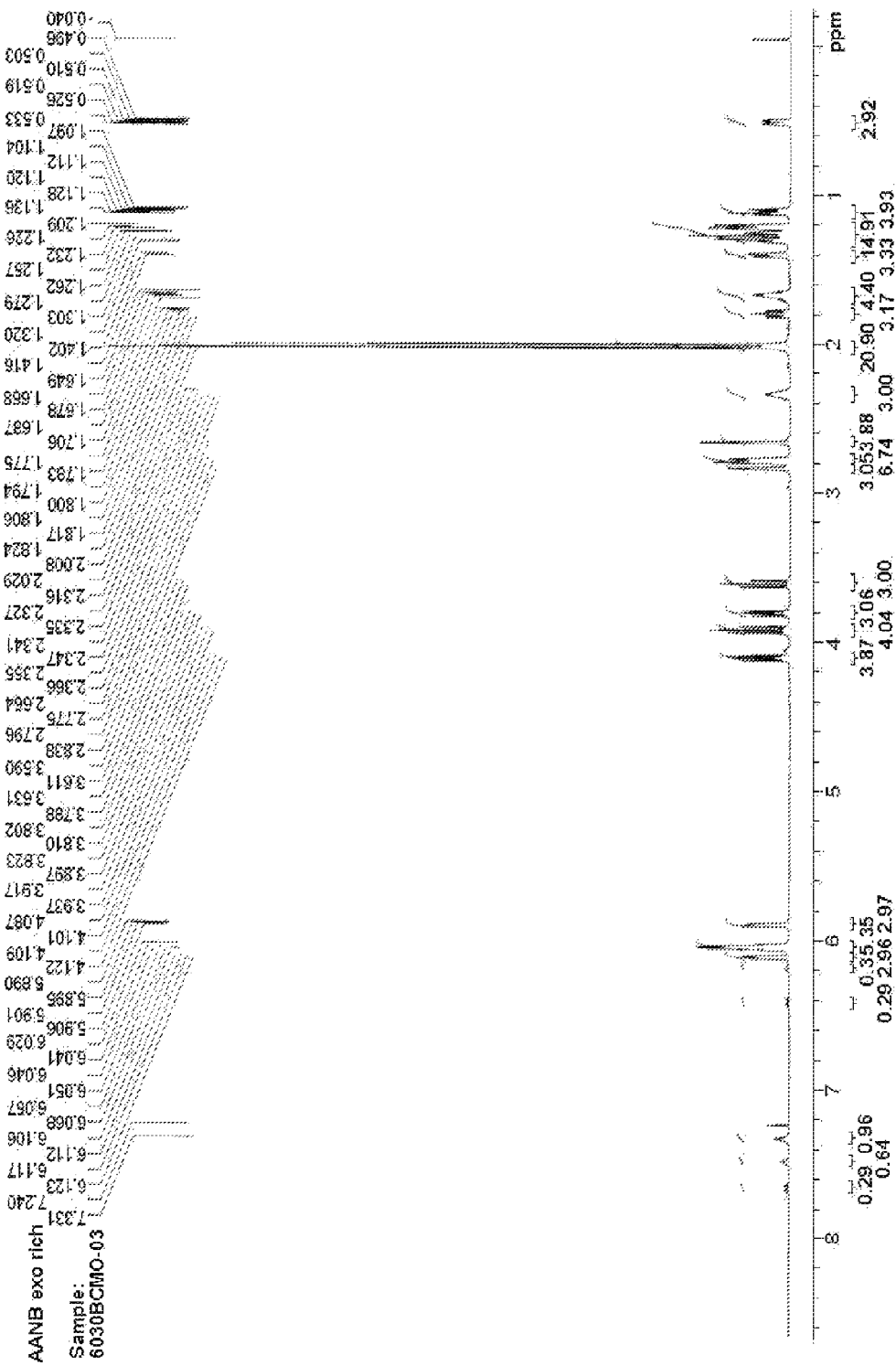
[Figure 3]

[Figure 4]
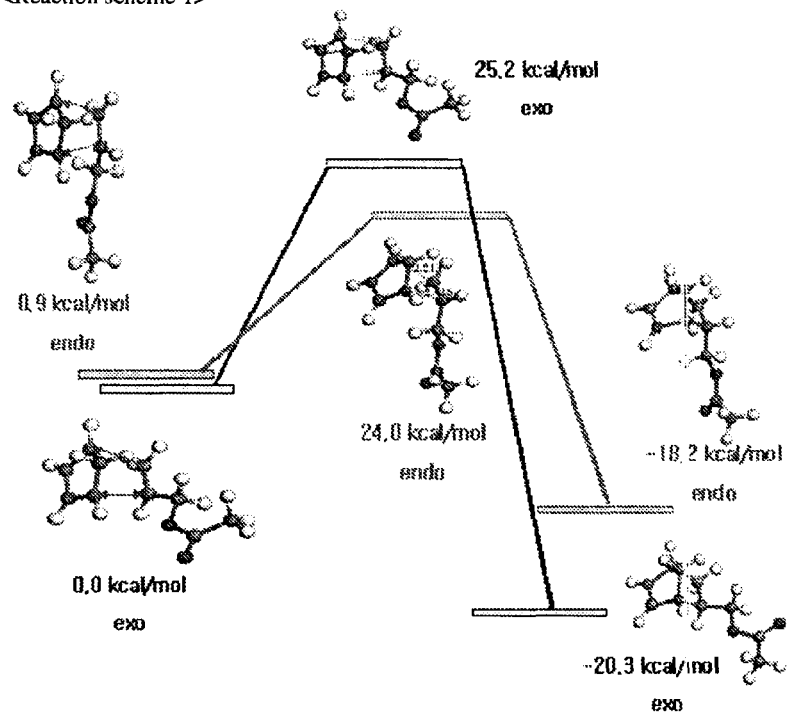

[Figure 5]
<Reaction scheme 2>
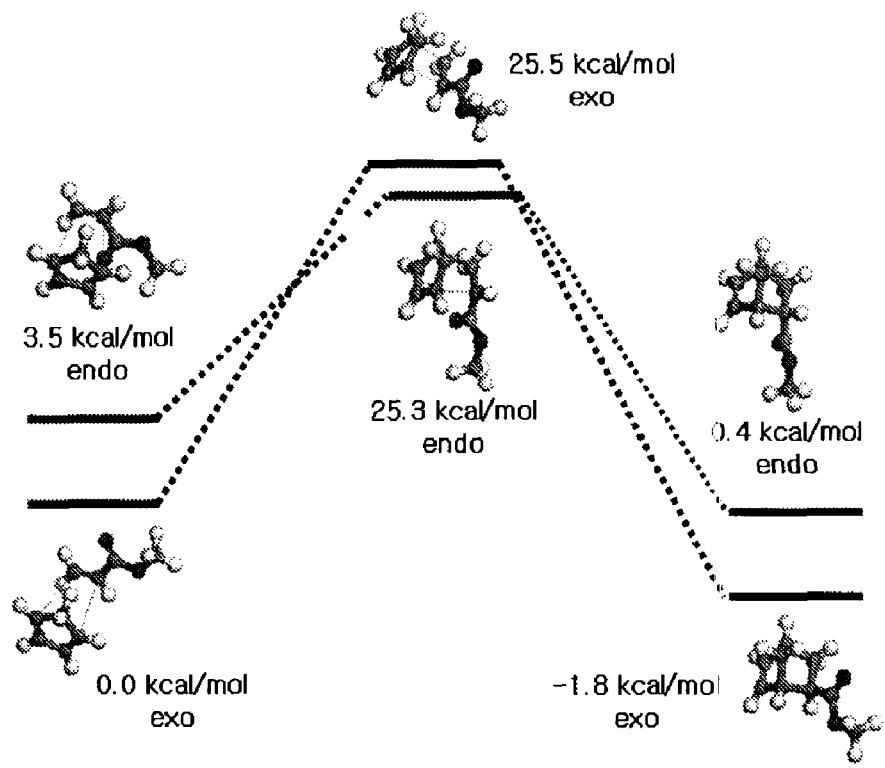

METHOD FOR PREPARING NORBORNENE MONOMER COMPOSITION, NORBORNENE POLYMER PREPARED THEREFROM, OPTICAL FILM COMPRISING THE NORBORNENE POLYMER, AND METHOD FOR PREPARING THE NORBORNENE POLYMER

This application claims the benefit of PCT/KR2007/003104 filed on Jun. 26, 2007 and also Korean Patent Application No. 10-2006-0057627 filed on Jun. 26, 2006, the contents of which are hereby incorporated herein by reference for all purposes in their entirety.

TECHNICAL FIELD

The present invention relates to a method for producing a norbornene monomer composition, a norbornene polymer produced using the norbornene monomer composition, an optical film including the norbornene polymer, and a method for producing the norbornene polymer. More particularly, the present invention relates to a method for producing a polar norbornene monomer composition that contains an exo isomer in content of 50 mol % or more, a norbornene polymer produced using the method, an optical film including the norbornene polymer, and a method for producing the norbornene polymer.

BACKGROUND ART

A thermoplastic norbornene addition polymer that includes a polar functional group is transparent and has low dielectric constant and hygroscopic property. Furthermore, the norbornene addition polymer is excellent in terms of thermal stability, mechanical strength, and adhesion strength, and generates no byproducts when bring attached to metal or other polymers. The norbornene addition polymer may be used in a polarizer protection film, an optical film such as a retardation film, a plastic substrate material, a transparent polymer such as POF, a PCB, or an insulating electronic material such as an insulating substance.

However, when an addition polymer is produced by using a norbornene monomer having a polar functional group, in the case where the monomer is the endo isomer, a polymerization speed is lower, a polymer has a lower molecular weight, and a polymerization yield is lower as compared to the case where the monomer is the exo isomer.

For example, according to Risse et al., if a norbornene derivative having a polar functional group such as an ester group is produced by using a palladium catalyst ($Pd(CH_3CN)_4$)[$BF_4$]$_2$), in the case where the ratio of endo isomer is higher among exo and endo isomers of the ester-norbornene monomer (exo/endo=20/80 and yield 23 to 30%), the polymerization yield and the molecular weight are lower as compared to the case where polymerization is performed by using only the exo isomer (yield 70% or more) ((a) Risse et al.; Makromol. Chem., 1992, Vol. 193, 2915-2927; (b) Risse et al.; Macromolecules, 1996, Vol. 29, 2755-2763).

The reason why the polymerization yield and the molecular weight are lower is that unshared electron pairs of the polar functional group of the endo type substituent are strongly bonded to vacant sites of a metal catalyst to prevent the norbornene monomers from approaching the metal, thereby slowing down the polymerization. For example, in the case where norbornene has an endo type ester group, a complex is stabilized and the unshared electron pairs of the oxygen atom partially provide electrons to the metal atom due to a chelate effect where an oxygen atom of a carbonyl group that is contained in the ester group is bonded to a metal catalyst. Thus, a catalytic activity of the metal atom is reduced (a) Sen et al.; Organometallics 2004, 23, 1680-1683; (b) Sen et al.; Organometallics 2001, 20, 2802-2812; (c) Sen et al.; Acc. Chem. Res. 1993, 26, 303-310; (d) Risse et al. Macromolecules 1995, 29, 2755-2763.).

Accordingly, in the addition polymerization of the norbornene monomer having the polar functional group, only the exo isomer may be used or the monomer that contains the exo isomer in a large amount (an excessive amount of exo) may be used to significantly increase the molecular weight while the yield is not reduced during the production of the polymer. In addition, in the case where a film is produced by using the above-mentioned polymer, viscosity of a film production solution is increased, the modulus of the film is improved, and surface hardness is improved. Hence, it is possible to produce a film having excellent mechanical properties. Therefore, it is very important to ensure a reaction condition capable of controlling a ratio of norbornene isomers (endo and exo isomers).

However, a known method for producing a norbornene monomer having a polar functional group by using a catalyst such as a Lewis acid is problematic in that an endo isomer is generated in a large amount (Chem. Rev. 1961, 61, 537-562).

For example, in the case of a 5-norbornene-2-methyl acetate monomer, a production method by using norbornene methanol (bicyclo[2.2.1]hept-5-enyl-2-methanol) is known in the art. However, a plurality of stages are performed in the method, and the resulting compound contains the large amount of endo isomer so that a ratio of exo/endo isomers is 20/80 ((a) Castner, K. F.; Calderon, N. J. Mol. Catal. 1982, 15, 47.; (b) Risse et al.; Makromol. Chem. 1992, 193, 2915. (c) Roberts et al.;. J. Am. Chem. Soc. 1950, 72, 3116. (d) Ver Nooy et al. J. Am. Chem. Soc. 1955, 77, 3586. (e) Arjona et al. J. Org. Chem. 1991, 56, 6227. (f) Nelson et al. Synthesis 1975, 105. (g) Magoon et al. J. Organomet. Chem. 1973, 55, 409.).

That is, it is difficult to achieve synthesis of a pure exo isomer of 5-norbornene-2-methyl acetate by using a simple process, and a plurality of stages must be performed in known processes. Accordingly, there is a need to provide a method of industrially producing a norbornene monomer containing an excessive amount of exo isomer by using a simple process.

It is known that a sterical chemical of a product depends on polar or nonpolar properties of a solvent in a Diels-Alder reaction (Otto et al.; J. Am. Chem. Soc. 1996, 118, 7702). However, a ratio of an exo isomer product to an endo isomer product is not more than 33%.

Therefore, there remains a need to provide a method of industrially producing a norbornene monomer that is used to produce an addition polymer of the norbornene monomer having a polar functional group, has the polar functional group, and contains an excessive amount of exo isomer by using a simple process so that the yield of polymer is improved and the molecular weight is increased.

DISCLOSURE

Technical Problem

An object of the present invention is to provide a method for producing an acetate norbornene monomer composition containing an exo isomer in content of 50 mol % or more. The method includes controlling variables such as a reaction temperature, a reaction time, a molar ratio between reactants, and addition of a solvent while a catalyst is not added.

Another object of the present invention is to provide a norbornene polymer produced using an acetate norbornene monomer composition containing an exo isomer in content of 50 mol % or more.

Still another object of the present invention is to provide an optical film including the norbornene polymer.

Yet another object of the present invention is to provide a method for producing the norbornene polymer.

Technical Solution

The present invention provides a method for producing a norbornene monomer composition. The method includes reacting a reaction solution that contains cyclopentadiene, dicyclopentadiene, or a mixture of cyclopentadiene and dicyclopentadiene, a compound represented by Formula 1, and a solvent at a reaction temperature of 230 to 330° C. for a reaction time of 0.1 to 24 hours so that a content of an exo isomer is 50 mol % or more.

    $CH_2=CH-(CH_2)_n-OC(O)R$    <Formula 1> wherein n is an integer of 0 to 10, and R is an alkyl group having 1 to 20 carbon atoms.

Advantageous Effects

According to the present invention, in order to produce an acetate norbornene monomer composition containing an exo isomer in content of 50 mol % or more, variables such as a reaction temperature, a reaction time, a molar ratio between reactants, and addition of a solvent are controlled. Thus, it is possible to industrially produce the acetate norbornene monomer composition, a norbornene polymer produced using the composition, and an optical film including the polymer using an easy process.

DESCRIPTION OF DRAWINGS

FIG. 1 is an NMR spectrum of a pure exo isomer of 5-norbornene-2-methyl acetate;

FIG. 2 is an NMR spectrum of a pure endo isomer of 5-norbornene-2-methyl acetate; and FIG. 3 is an NMR spectrum of 5-norbornene-2-methyl acetate produced in Example 9.

FIG. 4 is an reaction scheme 1.

FIG. 5 is an reaction scheme 2.

BEST MODE

The present invention provides a method for producing a norbornene monomer composition. The method includes reacting a reaction solution that contains cyclopentadiene, dicyclopentadiene, or a mixture of cyclopentadiene and dicyclopentadiene; a compound represented by Formula 1; and a solvent; at a reaction temperature of 230 to 330° C. for a reaction time of 0.1 to 24 hours so that a content of an exo isomer is 50 mol % or more.

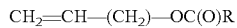    $CH_2=CH-(CH_2)-OC(O)R$    <Formula 1> wherein n is an integer of 0 to 10, and R is an alkyl group having 1 to 20 carbon atoms.

Furthermore, the present invention provides a norbornene polymer including a repeating unit that is represented by Formula 2 and contains an exo isomer in a content of 50 mol % or more.

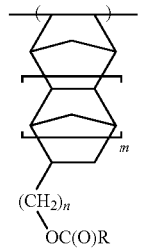

<Formula 2> wherein m is an integer of 0 to 4, n is an integer of 0 to 10, and R is an alkyl group having 1 to 20 carbon atoms.

Furthermore, the present invention provides an optical film including the norbornene polymer.

Furthermore, the present invention provides a method for producing a norbornene polymer that is represented by Formula 5. The method includes bringing a reactant that contains a norbornene monomer composition having an exo isomer in a content of 50 mol % or more into contact with a catalyst of a transition metal of Group 10.

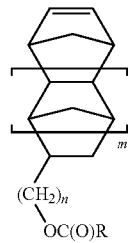

<Formula 5> wherein m is an integer of 0 to 4, n is an integer of 0 to 10, and R is an alkyl group having 1 to 20 carbon atoms.

Hereinafter, the present invention will be described in more detail.

Unlike a known method where a polar norbornene monomer composition containing an exo isomer in content of 50 mol % or more is produced through a complicated process, the present invention provides a method for producing an acetate norbornene monomer composition containing an exo isomer in content of 50 mol % or more, which includes controlling variables such as a reaction temperature, a reaction time, a molar ratio between reactants, and addition of a solvent while a catalyst is not added, a norbornene polymer produced using the norbornene monomer composition, an optical film including the norbornene polymer, and a method for producing the norbornene polymer.

In order to confirm a difference in physical properties of an endo isomer and an exo isomer used in the present invention, the pure endo isomer and the pure exo isomer were produced by using a known method to ensure different polymerization activities according to the type of isomer. In addition, a difference in molecular weight of the polymer that is produced by using the isomers was confirmed.

It is difficult to obtain the pure exo isomer or the endo isomer of 5-norbornene-2-methyl acetate by a simple synthesis method, and a plurality of steps must be performed in the known process.

<Pre-Test to Confirm a Difference in Physical Properties of the Endo Isomer and the Exo Isomer>

Each of the pure exo isomers and the pure endo isomers of 5-norbornene-2-methyl acetate were polymerized by using a {[Allyl(PdCl)]$_2$+AgSbF$_6$}catalyst that was disclosed in the paper set forth by Risse et al., thereby the fact that the molecular weights and the polymerization activities of the addition polymers were different from each other according to the type of isomer was confirmed.

FIG. 1 is an NMR spectrum of a pure exo isomer of 5-norbornene-2-methyl acetate, and FIG. 2 is an NMR spectrum of a pure endo isomer of 5-norbornene-2-methyl acetate.

In the present invention, in the case of the pure exo isomer monomer, the viscosity was significantly increased after 7 min, to render the polymerization reaction finished. However, in the case of the pure endo isomer monomer, the viscosity of the reaction solution was not significantly increased even though the reaction was performed for 4 hours.

The yield of the addition polymer of the pure exo isomer monomers in the case where the reaction was finished after 15 min was 95.5% and the yield of the addition polymer of the pure endo isomer monomers in the case where the reaction was finished after 4 hours was 64.0%. Thus, there was a significant difference in yield.

In addition, the number average molecular weight (Mn) of the addition polymer of the pure endo isomer monomers was about 24.1 K/mol, but the number average molecular weight (Mn) of the addition polymer of the pure exo isomer monomers was about 219.4 K/mol. Hence, it could be seen that the number average molecular weight of the addition polymer of the pure exo isomer monomers was 9 times as high as that of the addition polymer of the pure endo isomer monomers.

Furthermore, an optical isotropic film was produced by using the above-mentioned polymer to measure physical properties. Thereby, it could be seen that the optical and mechanical properties of the film that is produced by using the addition polymer varied according to the type of isomer.

Therefore, it can be seen that the physical properties significantly depend on the type of isomer and it is very important to provide an excessive amount of exo isomer in views of mass production.

The present invention provides a method for producing a norbornene monomer composition. The method includes reacting a reaction solution that contains cyclopentadiene, dicyclopentadiene, or a mixture of cyclopentadiene and dicyclopentadiene; a compound represented by Formula 1; and a solvent; at a reaction temperature of 230 to 330° C. for a reaction time of 0.1 to 24 hours so that a content of an exo isomer is 50 mol % or more.

<Formula 1> wherein n is an integer of 0 to 10, and R is an alkyl group having 1 to 20 carbon atoms.

Based on the fact that a Diels-Alder reaction is a reversible reaction, a reaction temperature was set to be high and a solvent was used in order to produce a large amount of thermodynamically stable exo isomers when cyclopentadiene and the compound represented by Formula 1 are reacted with each other, thereby the present invention was accomplished.

The reason why the exo isomer is contained in content of 50 mol % or more will be described below. This description are set forth to illustrate, but are not to be construed to limit the present invention.

From comparison of reaction energies of the endo isomer and the exo isomer having an acetate functional group in the Diels-Alder reaction, the following fact can be known.

In the case where 5-norbornene-2-methyl acetate is produced through the Diels-Alder reaction of cyclopentadiene (Cp) and allyl acetate, the energy of the transition state and the energy of the reaction product are as shown in Reaction scheme 1 in FIG. 4.

In views of the energy of the transition state of the production reaction, the endo isomer is more stable than the exo isomer by about 1.2 kcal/mol. However, in views of the energy of the reaction product, the exo isomer is more stable than the endo isomer by about 2.1 kcal/mol. This can be confirmed by using the DFT (Density functional theory) calculation. The detailed description of the calculation is given in Calculation example 1.

Accordingly, in views of reaction kinetics, since the transition state of the endo isomer is stable, the endo isomer is competitive in terms of energy in the Diels-Alder reaction. Thus, the endo isomer can be easily produced. In views of thermodynamics, since the reaction product of the exo isomer is stable, the exo isomer is competitive in terms of energy in the Diels-Alder reaction. Hence, in the case where the reaction time and the reaction temperature are controlled to form a state that is useful to produce thermodynamically stable isomers, monomers that consist mostly of the exo isomers can be synthesized.

In the Diels-Alder reaction where the polar functional group is used, it is more difficult to react an acetyl group and cyclopentadiene to form the exo isomer in comparison with an ester group. The reason can be seen by comparison of reaction energies of the endo isomer and the exo isomer.

For example, in the case where methyl ester norbornene is produced by using the Diels-Alder reaction of cyclopentadiene and methyl acrylate, the energy of the transition state and the energy of the reaction product in the reaction are as shown in Reaction scheme 2 in FIG. 5.

That is, in the production reaction of the ester norbornene, a difference in energy of the transition state of the exo isomer and the endo isomer is about 0.2 kcal/mol. However, in the production reaction of the acetate norbornene (5-nonbornene-2-methyl acetate) (<Reaction scheme 1>), a difference in energy of the transition state of the exo isomer and the endo isomer is about 1.2 kcal/mol which is higher than that of the case of the production reaction of the ester norbornene.

That is, in the acetyl group, stability of the transition state of the endo isomer is still higher than that of the exo isomer in comparison with that in the ester group. However, a difference in energy of the exo isomer and the endo isomer of the reaction product is about 2.2 kcal/mol in the case of the ester group and about 2.1 kcal/mol in the case of the acetyl group. Thus, the exo isomer is insignificantly different from the endo isomer in terms of the difference in energy of the reaction product.

In the case of dicyclopentadiene, a ring-opening reaction occurs in the range of the reaction temperature to convert dicyclopentadiene into cyclopentadiene, and the subsequent reaction may be progresses according to the same mechanism as cyclopentadiene.

A ratio of the exo/endo isomers that are generated during a Diels-Alder reaction is known to be changed according to the polarity of a solvent (Otto et al.; J. Am. Chem. Soc. 1996, 118, 7702).

However, the cited document does not suggest the condition that content of the exo isomer is 50 mol % or more. Accordingly, it can be seen that it is difficult to increase the relative amount of the exo isomer by changing only the polarity of the solvent.

In the method for producing the monomer composition according to the present invention, examples of the solvent include, but are not limited to cyclohexane, toluene, acetone, methyl ethyl ketone (MEK), ethyl acetate, dimethyl sulfoxide (DMSO), tetrahydrofuran (THF), dimethyl formamide (DMF), and a mixture thereof.

In addition, the present invention provides a method for producing a norbornene monomer composition so that content of the exo isomer is 50 mol % or more by using a change in temperature as well as polarity of the solvent.

In the present invention, in order to produce the norbornene monomer containing the excessive amount of exo isomer having the polar functional group, the reaction temperature is preferable 230 to 330° C. and more preferably 270 to 330° C. In the case where the reaction temperature is lower than 230° C., it is impossible to produce the norbornene monomer containing the excessive amount of exo isomer having the polar functional group. In the case where the reaction temperature is higher than 330° C., there is a problem in that the production yield of monomer is reduced due to increased byproducts or decomposition of products.

Additionally, in the present invention, since the reaction temperature is maintained at about 230° C. or more, instead of cyclopentadiene that is one of raw materials used to produce the norbornene monomer, more stable dicyclopentadiene can be used.

Since cyclopentadiene is unstable at normal temperature and thus easily converted into dicyclopentadiene, it is difficult to maintain pure cyclopentadiene. However, dicyclopentadiene is decomposed at 180° C. or more to participate in the reaction while dicyclopentadiene is divided into two cyclopentadiene molecules. Thus, in the present invention, both cyclopentadiene and dicyclopentadiene are capable of being used as raw materials of the reaction. Accordingly, since it is unnecessary to purify cyclopentadiene from dicyclopentadiene, there is an advantage in that the production process is simple.

Furthermore, although the reaction is not affected by the pressure, an increase in pressure may occur due to vaporization of the reactants at high temperatures during the reaction and the reaction may be performed in the range of 1 to 30 atm.

Additionally, the reaction time may be in the range of 5 min to 24 hours, preferably 5 min to 16 hours, and more preferably 5 min to 5 hours. This is because the reaction time affects the degree of reaction and a change in selectivity. That is, in the reaction in the range of 5 min or less, even though the reaction temperature is increased to 330° C., it is difficult to obtain the compound containing the excessive amount of exo isomer. If the reaction time is 24 hours or more, it is possible to obtain the compound containing the excessive amount of exo isomer but many side reactions occur, which reduces the yield.

In respects to the correlation of the reaction temperature and the reaction time, it is preferable to perform the reaction so that the reaction quotient represented by the following Equation 1 be 25,200 to 350,000.

Reaction quotient=reaction temperature (° C.)$^2$×log (reaction time (min))  <Equation 1>

That is, in the case where the reaction is performed at the temperature in the range of 230 to 330° C. which satisfies the above-mentioned reaction temperature condition, it is preferable that the reaction be performed so that the above-mentioned reaction index is satisfied in order to increase the content of exo isomer and the production yield of the monomer.

In the production method according to the present invention, the molar ratio of the compound represented by Formula 1 to cyclopentadiene, dicyclopentadiene, or a mixture thereof among the above-mentioned reactants may be in the range of 1:0.1 to 1:10, preferably 1:0.5 to 1:10, and more preferably 1:0.5 to 1:5. This is because the molar ratio depends on the degree of reaction and the selectivity.

In the case where the molar ratio of the compound represented by Formula 1 is 1:1 or more, the acetate norbornene monomer composition where m is 0 in Formula 5 is generated as a main product. In the case where the molar ratio is less than 1:1, the acetate norbornene monomer composition where m is 1 to 4 in Formula 5 is generated as a main product.

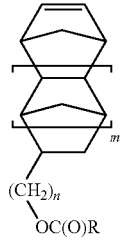

<Formula 5> wherein m is an integer of 0 to 4, n is an integer of 0 to 10, and R is an alkyl group having 1 to 20 carbon atoms.

Additionally, in the production method according to the present invention, in order to prevent the reactants and the products from being polymerized or decomposed during the reaction, it is preferable to add a polymerization inhibitor during the reaction.

Examples of the polymerization inhibitor include, but are not limited to one or more compounds selected from the group consisting of aniline, cyclohexane, phenol, 4-ethoxyphenol, nitrobenzene, hydroquinone, benzoquinone, copper dichloride, and 2,2-di(4-tert-octylphenyl)-1-picrylhydrazyl, and Irganox.

Specific examples of Irganox may include Irganox 1010, Irganox 1035, Irgarnox 1076, Irganox 1081, Irganox 1098, Irganox 1135, Irganox 1330, Irganox 1520, Irganox 1726, and Irganox 245.

Additionally, in the production method of the monomer composition according to the present invention, it is preferable that a weight ratio of the polymerization inhibitor to the total weight of the reactant such as cyclopentadiene (Cp), dicyclopentadiene (DCPD), or a mixture thereof, and the compound represented by Formula 1 be in the range of 1:0.0001 to 1:10. In the case where the weight ratio is less than 1:0.0001, it is impossible to efficiently prevent self-polymerization of the reactant (Cp or DCPD). Even though the weight ratio is 1:10, the function of the polymerization inhibitor is sufficiently realized.

That is, even though the amount of polymerization inhibitor is increased, the increased amount does not affect the yield. In the case where the large amount of inhibitor is used, there is a problem in that it is necessary to remove the polymerization inhibitor after the synthesis is finished. However, in the present invention, addition of the polymerization inhibitor is not essential.

Meanwhile, in the case where n is in the range of 0 in Formula 1, the above-mentioned norbornene monomer composition may contain 50 to 100 mol % of exo isomer. In the case where n is in the range of 1 to 10, the norbornene monomer composition may contain 50 to 90 mol % of exo isomer, but the content is not limited thereto.

The present invention provides a norbornene polymer including a repeating unit that is represented by Formula 2 and contains an exo isomer in a content of 50 mol % or more.

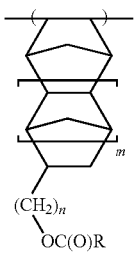

<Formula 2> wherein m is an integer of 0 to 4, n is an integer of 0 to 10, and R is an alkyl group having 1 to 20 carbon atoms.

In connection with this, in the case of norbornene polymer, n is 0 and the content of the exo isomer in the repeating unit is 50 to 100 mol %. Alternatively, in the norbornene polymer, n is in the range of 1 to 10 and the content of the exo isomer in the repeating unit is 50 to 90 mol %.

The degree of polymerization of the norbornene polymer is in the range of preferably 10 to 20,000 and more preferably 10 to 10,000.

Hereinafter, specific embodiments of the norbornene polymer according to the present invention will be described. The embodiments are set forth to illustrate, but are not to be construed to limit the present invention.

According to a first embodiment of the present invention, the above-mentioned norbornene polymer may be a homopolymer containing a repeating unit selected from the compounds represented by Formula 2.

According to a second embodiment of the present invention, the above-mentioned norbornene polymer may be a copolymer containing at least two repeating units selected from the compounds represented by Formula 2.

According to a third embodiment of the present invention, the above-mentioned norbornene polymer may be a copolymer further containing a polar norbornene repeating unit of Formula 3, if necessary.

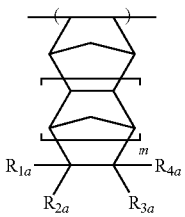

<Formula 3> wherein m is an integer of 0 to 4, at least one of $R_{1a}$, $R_{2a}$, $R_{3a}$, and $R_{4a}$ is a polar functional group containing at least one atom selected from the group consisting of oxygen, nitrogen, phosphorus, sulfur, silicon, and boron, and $R_{1a}$, $R_{2a}$, $R_{3a}$, and $R_{4a}$ that are not the polar functional group are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1a}$ and $R_{2a}$ or $R_{3a}$ and $R_{4a}$ and has 1 to 10 carbon atoms; a saturated or unsaturated cyclic group that is formed by bonding of $R_{1a}$ or $R_2$ to either of $R_{3a}$ and $R_{4a}$ and has 4 to 12 carbon atoms; or an aromatic cyclic compound that has 6 to 24 carbon atoms.

According to a fourth embodiment of the present invention, the above-mentioned norbornene polymer may be a copolymer further containing a nonpolar norbornene repeating unit of Formula 4, if necessary.

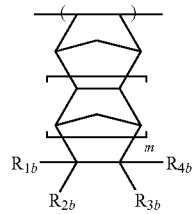

<Formula 4> wherein m is an integer of 0 to 4, and $R_{1b}$, $R_{2b}$, $R_{3b}$, and $R_{4b}$ are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1b}$ and $R_{2b}$ or $R_{3b}$ and $R_{4b}$ and has 1 to 10 carbon atoms; a saturated or unsaturated cyclic group that is formed by bonding of $R_{1b}$ or $R_{2b}$ to either of $R_{3b}$ and $R_{4b}$ and has 4 to 12 carbon atoms; or an aromatic cyclic compound that has 6 to 24 carbon atoms.

According to a fifth embodiment of the present invention, the above-mentioned norbornene polymer may be a copolymer further containing a polar norbornene repeating unit of Formula 3 and a nonpolar norbornene repeating unit of Formula 4, if necessary.

In the copolymer according to the third embodiment and the fifth embodiment, examples of the polar functional group that is contained in the polar norbornene repeating unit of Formula 3 include —C(O)OR$_6$, —R$_5$C(O)OR$_6$, —OR$_6$, —R$_5$OR$_6$, —OC(O)OR$_6$, —R$_5$OC(O)OR$_6$, —C(O)R$_6$, —R$_5$C(O)R$_6$, —OC(O)R$_6$, —R$_5$OC(O)R$_6$, —(R$_5$O)$_p$—OR$_6$, —(OR$_5$)$_p$—OR$_6$, —C(O)—O—C(O)R$_6$, —R$_5$C(O)—O—C(O)R$_6$, —SR$_6$, —R$_5$SR$_6$, —SSR$_6$, —R$_5$SSR$_6$, —S(=O)R$_6$, —R$_5$S(=O)R$_6$, —R$_5$C(=S)R$_6$, —R$_5$C(=S)SR$_6$, —R$_5$SO$_3$R$_6$, —SO$_3$R$_6$, —R$_5$N=C=S, —N=C=S, —NCO, R$_5$—NCO, —CN, —R$_5$CN, —NNC(=S)R$_6$, —R$_5$NNC(=S)R$_6$, —NO$_2$, —R$_5$NO$_2$,

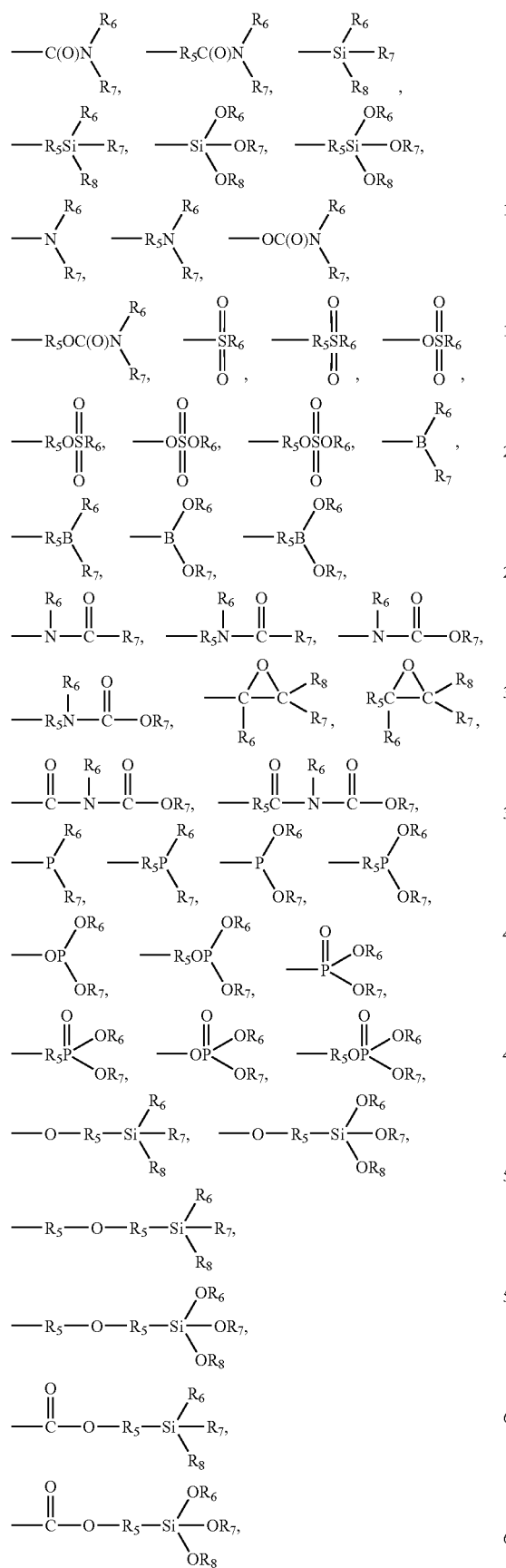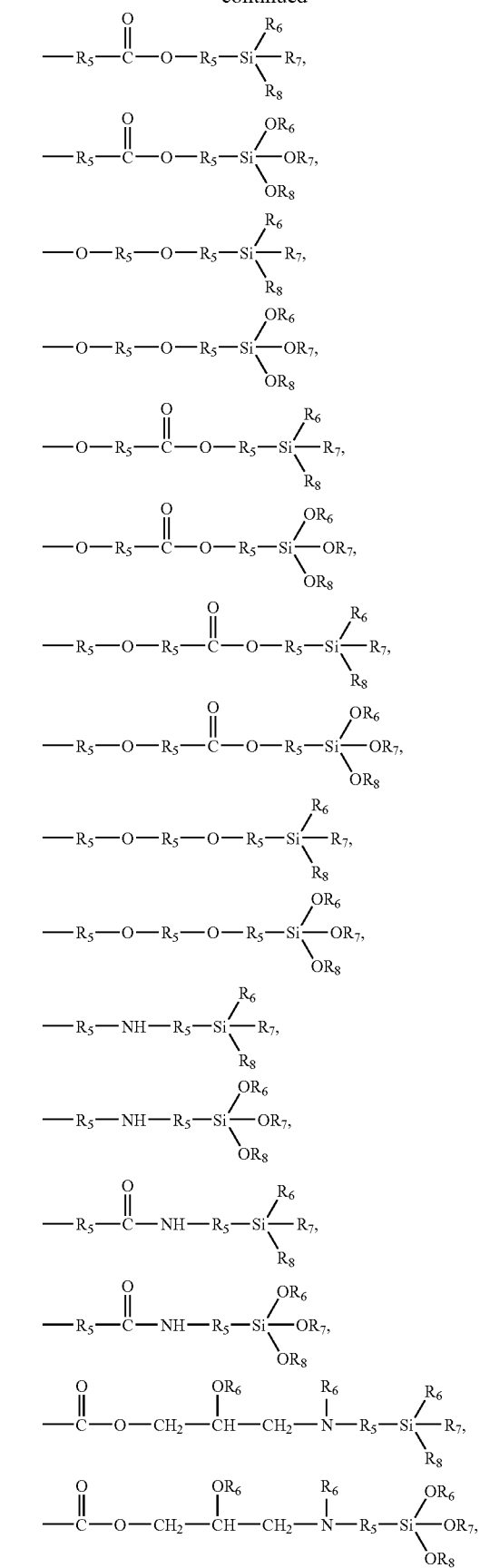

-continued

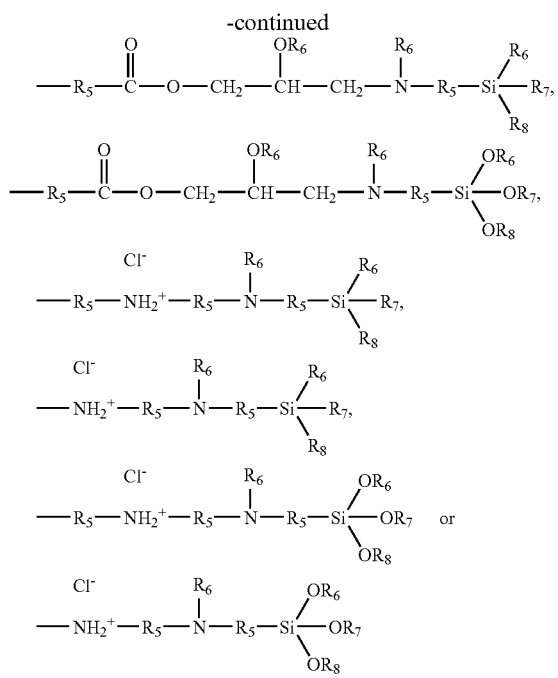

wherein each $R_5$ is independently linear or branched alkylene, haloalkylene, alkenylene, haloalkenylene, vinylene, or halovinylene that has 1 to 20 carbon atoms; cycloalkylene or halocycloalkylene that is substituted or unsubstituted with hydrocarbon and has 4 to 12 carbon atoms; arylene or haloarylene that is substituted or unsubstituted with hydrocarbon and has 6 to 40 carbon atoms; aralkylene or haloaralkylene that is substituted or unsubstituted with hydrocarbon and has 7 to 15 carbon atoms; or alkynyklne or haloalkynylene that has 3 to 20 carbon atoms, each $R_6$, $R_7$, and $R_8$ are independently hydrogen; halogen; linear or branched alkyl, haloalkyl, alkenyl, haloalkenyl, vinyl, halovinyl, alkoxy, haloalkoxy, carbonyloxy, or halocarbonyloxy that has 1 to 20 carbon atoms; cycloalkyl or halocycloalkyl that is substituted or unsubstituted with hydrocarbon and has 4 to 12 carbon atoms; aryl, haloaryl, aryloxy, or haloaryloxy that is substituted or unsubstituted with hydrocarbon and has 6 to 40 carbon atoms; aralkyl or haloaralkyl that is substituted or unsubstituted with hydrocarbon and has 7 to 15 carbon atoms; or alkynyl or haloalkynyl that has 3 to 20 carbon atoms, and each p is independently an integer of 1 to 10.

In the copolymer according to the third embodiment, the molar ratio of the acetate norbornene repeating unit of Formula 2 and the polar norbornene repeating unit of Formula 3 depends on the required physical properties of the polymer, and a polymerization activity is improved as the content of the repeating unit of Formula 2 is increased. Accordingly, the molar ratio of the repeating units of Formulae 2 and 3 is in the range of preferably 1:700 to 700:1 and more preferably 1:100 to 100:1.

In the copolymer according to the fourth embodiment, the molar ratio of the acetate norbornene repeating unit of Formula 2 and the nonpolar norbornene repeating unit of Formula 4 depends on the required physical properties of the polymer. Because of the same reason, the molar ratio of the repeating units of Formulae 2 and 4 is preferably 1:700 to 700:1 and more preferably 1:100 to 100:1.

Furthermore, in the copolymer according to the fifth embodiment, the molar ratio of the acetate norbornene repeating unit of Formula 2 and the repeating units of Formulae 3 and 4 depends on the required physical properties of the polymer. Because of the same reason, it is preferable that the molar ratio of the repeating unit of Formula 2 and the sum of the repeating units of Formulae 3 and 4 be 1:1,400 to 1,400:1 and the molar ratio of the polar repeating unit of Formula 3 and the nonpolar repeating unit of Formula 4 be 1:700 to 700:1. It is more preferable that the molar ratio of the repeating unit of Formula 2 and the sum of the repeating units of Formulae 3 and 4 be 1:500 to 500:1 and the molar ratio of the polar repeating unit of Formula 3 and the nonpolar repeating unit of Formula 4 be 1:100 to 100:1.

The present invention provides an optical film that includes the norbornene polymer.

Preferable examples of the optical film include, but are not limited to a polarizer protection film for LCDs or a plastic substrate that is a substitute for a glass substrate, and the optical film may be used as various types of optical materials within the scope of the present invention.

Specifically, it is preferable that the optical film have the optical anisotropic property so that the retardation value ($R_{th}$) represented by Equation 1 is 70 to 1000 nm.

$$R_{th} = \Delta(n_y - n_z) \times d \qquad \text{<Equation 1>}$$

wherein $n_y$ is an in-plane refractive index of a fast axis that is measured at a wavelength of 550 nm, $n_z$ is a thickness refractive index that is measured at a wavelength of 550 nm, and d is a thickness of a film.

In addition, preferably, the optical film is a negative C-plate type optical compensation film for liquid crystal displays (LCDs) satisfying a refractive index correlation where $n_x \approx n_y > n_z$ ($n_x$ is an in-plane refractive index of a slow axis, $n_y$ is the refractive index of a fast axis, and $n_z$ is a thickness refractive index).

Furthermore, the present invention provides a method for producing a norbornene polymer that is represented by Formula 5. The method includes bringing a reactant that contains a norbornene monomer composition having an exo isomer in a content of 50 mol % or more into contact with a catalyst of a transition metal of Group 10.

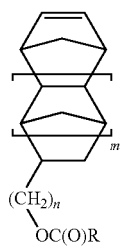

<Formula 5> wherein m is an integer of 0 to 4, n is an integer of 0 to 10, and R is an alkyl group having 1 to 20 carbon atoms.

Examples of the catalyst of the transition metal of Group 10 may include a known catalyst for cyclic olefin polymerization used in the art such as a Pd metal catalyst. Like a known polymerization method, since the above-mentioned polymer system is produced by mixing monomers to be polymerized, a catalyst, and a solvent and polymerizing the resulting reaction mixture, it is not limited thereto.

In the method for producing the norbornene polymer, the monomer composition contains only any one monomer selected from the compounds of Formula 5, but is not limited thereto. The monomer composition may contain at least two monomers selected from the compounds of Formula 5 to remove the copolymer according to the second embodiment, or may contain the polar norbornene monomer of Formula 6, the nonpolar norbornene polymer of Formula 7, or the polar norbornene monomer and the nonpolar norbornene polymer to produce the copolymers of the third to fifth embodiments if necessary.

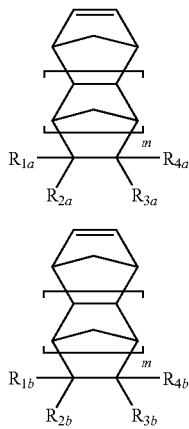

<Formula 6>

<Formula 7> wherein each m is independently an integer of 0 to 4, at least one of $R_{1a}$, $R_{2a}$, $R_{3a}$, and $R_{4a}$ is a polar functional group containing at least one atom selected from the group consisting of oxygen, nitrogen, phosphorus, sulfur, silicon, and boron, and $R_{1a}$, $R_{2a}$, $R_{3a}$, and $R_{4a}$ that are not the polar functional group are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1a}$ and $R_{2a}$ or $R_{3a}$ and $R_{4a}$ and has 1 to 10 carbon atoms; a saturated or unsaturated cyclic group that is formed by bonding of $R_{1a}$ or $R_{2a}$ to either of $R_{3a}$ and $R_{4a}$ and has 4 to 12 carbon atoms; or an aromatic cyclic compound that has 6 to 24 carbon atoms, and each $R_{1b}$, $R_{2b}$, $R_{3b}$, and $R_{4b}$ are independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1b}$ and $R_{2b}$ or $R_{3b}$ and $R_{4b}$ and has 1 to 10 carbon atoms; a saturated or unsaturated cyclic group that is formed by bonding of $R_{1b}$ or $R_{2b}$ to either of $R_{3b}$ and $R_{4b}$ and has 4 to 12 carbon atoms; or an aromatic cyclic compound that has 6 to 24 carbon atoms.

However, during the production of the copolymer according to the third to the fifth embodiments, the ratio of the monomers to be used may be controlled to be the same as the above-mentioned molar ratio of the repeating units of the copolymers.

Mode for Invention

A better understanding of the present invention may be obtained in light of the following Examples which are set forth to illustrate, but are not to be construed to limit the present invention.

EXAMPLE

All operations where compounds that are sensitive to air or water were treated were performed by using a standard Schlenk technique or a dry box technique.

The nuclear magnetic resonance (NMR) spectrum was obtained by using a Bruker 600 spectrometer and a Bruker 300 spectrometer. $^1$H NMR was measured at 600 MHz and 300 MHz and $^{13}$C NMR was measured at 150 MHz and 75 MHz.

In order to precisely distinguish NMR signals, various types of two-dimensional experiments such as COSY and HMBC were performed.

The molecular weight and the molecular weight distribution of the polymer were measured by using GPC (gel permeation chromatography), and a polystyrene sample was used as a standard. Gas chromatography (GC) equipment that was provided with a flame ionization detector (FID) and an AT1000 column was used.

Toluene was purified through distillation using potassium/benzophenone, and $CH_2Cl_2$ was distilled by using $CaH_2$ to be purified.

CALCULATION EXAMPLE

DTF (Density functional theory) calculation

In order to calculate the activation energy and the reaction energy of the exo and endo 5-norbornene-2-methyl acetate isomers, a BPW91 function (Perdew, J. P.; Wang, Y. Phys. Rev., B45, 13244 (1992); Becke, A. D. J. Chem. Phys., 88, 2547 (1988)) which was one of DFT functions was used. The basis set chosen was the double numerical plus d-functions (DNP) in order to confirm C, O, and H atoms.

Dmol3 (Delley B J. Chem. Phys. 92, 508, 1990; Delley B J. Chem. Phys. 94, 7245, 1991; Delley B J. Chem. Phys. 113, 7756, 2000), a commercial DFT program, was used as the program of the present invention.

In order to obtain the reaction energy and the transition state, the structures of the reactant and the product were optimized without any constraint.

From the energy data of the optimized reactant and product, the reaction energy was obtained. The structure of the transition state was obtained by means of an LST method (Complete Linear Synchronous Transit) using the structure estimated from the structures of the reactant and the product.

The calculation showed that the energy of the endo isomer was more stable by about 1.2 kcal/mol in the transition state and, in the case of the reaction product such as the 5-norbornene 2-methyl acetate molecule, the energy of the exo isomer was more stable by about 2.1 kcal/mol.

Production of an Acetate Norbornene Monomer Composition

Example 1

Dicyclopentadiene (DCPD, Maruzen, purity 99%, 66.1 g, and 0.5 mol), allyl acetate (AA, Showa Denko, 125.15 g, and 1.25 mol), and hydroquinone (HQ) acting as the polymerization inhibitor were added in an amount of (1.1 parts by weight based on 100 parts by weight of the total weight of DCPD and AA, and 1 mol of tetrahydrofuran (THF) acting as the solvent was also added to a 300 mL high pressure reactor. The reactants were agitated at normal pressure for 10 min so that the polymerization inhibitor was completely dissolved to desirably mix the reactants with each other, heated to 290° C., and agitated again at 300 rpm to perform the reaction for 3 hours.

After the reaction was finished, the temperature was reduced to normal temperature and the yellow or brown resulting solution was distilled to produce a 5-norbornene-2-methyl acetate monomer composition.

The reaction was performed in a nitrogen ($N_2$) atmosphere (vacuum distillation temperature: 50 to 70° C. (Bath) and 34 to 40° C. (Head)).

Examples 2 to 9 and Comparative Examples 1 to 3

The reaction was performed by using the same procedure as Example 1 to produce a 5-norbornene-2-methyl acetate monomer composition, except that the condition was set to be the same as that of Table 1.

The yield and the exo/endo ratio of the 5-norbornene-2-methyl acetate monomer composition that were produced in Examples 1 to 9 and Comparative examples 1 to 3 were measured by using the following methods, and the results are described in Table 1.

The yield of the product that was produced during the Diels-Alder reaction was obtained by using the weight of the product that was purified at reduced pressure, and the purity and the exo/endo ratio of the product were obtained by using gas chromatography equipment that was provided with a flame ionization detector (FID) and an AT1000 column.

FIG. 3 is an NMR spectrum of the 5-norbornene-2-methyl acetate monomer composition produced in Example 9.

TABLE 1

|  | Temp (° C.) | Time (min) | DCPD (mol) | AA (mol) | Solvent | Reaction quotient | Exo/Endo molar ratio |
|---|---|---|---|---|---|---|---|
| Example 1 | 290 | 180 | 0.5 | 1.25 | THF (1 mol) | 189668 | 50/50 |
| Example 2 | 310 | 20 | 0.5 | 1.25 | THF (1 mol) | 125029 | 51/49 |
| Example 1 | 330 | 5 | 0.5 | 1.25 | THF (1 mol) | 76118 | 55/45 |
| Example 4 | 270 | 180 | 3 | 7.5 | THF (1 mol) | 164409 | 50/50 |
| Example 5 | 290 | 60 | 3 | 7.5 | THF (1 mol) | 149542 | 50/50 |
| Example 6 | 290 | 60 | 3 | 1.5 | THF (1 mol) | 149542 | 52/48 |
| Example 7 | 270 | 240 | 0.5 | 1.25 | CyHex (1.25) | 173517 | 50/50 |
| Example 8 | 270 | 180 | 0.5 | 1.25 | Tol (1.25) | 164409 | 52/48 |
| Example 9 | 270 | 300 | 0.5 | 1.25 | Tol (1.25) | 180582 | 54/46 |
| Comparative Example 1 | 270 | 180 | 0.5 | 1.25 | — | 164409 | 47/53 |
| Comparative Example 2 | 210 | 180 | 0.5 | 1.25 | — | 99458 | 20.7/79.3 |
| Comparative Example 3 | 220 | 180 | 0.5 | 1.25 | — | 119303 | 33.2/67.8 |

In Table 1, THF is tetrahydrofuran, CyHex is cyclohexane, and Tol is toluene.

From the data of Examples 1 to 3 in Table 1, it could be seen that the reaction toward the exo isomer was thermodynamically favored as the temperature was raised; accordingly, the ratio of the thermodynamically stable exo isomer was increased.

In addition, from the data of Examples 8 and 9, it could be seen that the content of exo isomer was increased as the reaction time was increased under the same condition.

Furthermore, from the results of Example 8 and Comparative example 1, it could be seen that the solvent functioned to stabilize the exo isomer in the transition state to achieve the thermodynamically advantageous reaction of the exo isomer.

Production of a Norbornene Polymer

Example 10

Polymerization of 5-norbornene-2-acetate where exo/endo=100/0

5-norbornene-2-acetate (NB—O—C(O)—$CH_3$) where exo/endo=100/0 (2.0 g, 13.2 mmol, and NB denotes norbornene) and 6 ml of toluene were put into a 250 mL Schlenk flask.

1 mL of dichloromethane was added to palladium acetate (Pd(OAc)$_2$) (OAc=acetate, 1.8 mg, and 2.64 mmol) and tricyclohexylphosphoniium(tetrakis pentafluorophenyl)borate ([(Cy)$_3$PH][B(C$_6$F$_5$)$_4$]) (5.1 mg and 5.28 mol) to perform dissolution and the resulting solution was added to the monomer solution.

The reaction temperature was increased to 90° C. and agitation was performed for 20 hours. After the reaction for 20 hours, 20 ml of tetrahydrofuran (THF) was added to dilute the polymer solution having the high viscosity, and the diluted polymer solution was added to an excessive amount of ethanol to obtain a white copolymer precipitate.

The precipitate was filtered by using a glass funnel and the recovered copolymer was dried in a vacuum oven at 70° C. for 24 hours to obtain 1.82 g of 5-norbornene-2-acetate polymer (91 wt % on the basis of the total amount of the added monomers).

The polymer was dissolved in trichlorobenzene to measure the molecular weight. The weight average molecular weight (Mw) was 104,000, and Mw/Mn was 2.3.

Example 11

Polymerization of 5-norbornene-2-methyl acetate where exo/endo=54/46

5-norbornene-2-methyl acetate (NB—$CH_2$—O—C(O)—$CH_3$) where exo/endo=54/46 (20.775 g, 0.125 mol, and NB denotes norbornene) and toluene (62.3 g) were put into a 250 mL Schlenk flask.

1 mL of dichloromethane was added to palladium acetate (Pd(OAc)$_2$) (OAc=acetate, 1.9 mg, and 8 μmol) and tricyclohexylphosphonium(tetrakis pentafluorophenyl) borate ([(Cy)$_3$PH][B(C$_6$F$_5$)$_4$]) (16 mg and 17 mol) to perform dissolution and the resulting solution was added to the monomer solution. The reaction temperature was increased to 90° C. and agitation was performed for 18 hours. After the reaction for 18 hours, 62.3 g of toluene was added to dilute the polymer solution having the high viscosity, and the diluted polymer solution was added to an excessive amount of ethanol to obtain a white copolymer precipitate.

The precipitate was filtered by using a glass funnel and the recovered copolymer was dried in a vacuum oven at 70° C. for 24 hours to obtain 20.35 g of 5-norbornene-2-methyl acetate polymer (98 wt % on the basis of the total amount of the added monomers).

The polymer was dissolved in tetrahydrofuran (THF) to measure the molecular weight. The weight average molecular weight (Mw) of the polymer was 383,523, and Mw/Mn was 2.28.

Example 12

Polymerization of 5-norbornene-2-methyl acetate where exo/endo=70/30

5-norbornene-2-methyl acetate (NB—$CH_2$—O—C(O)—$CH_3$) where exo/endo=70/30 (2.06 g, 12.4 mmol, and NB denotes norbornene) and 6 mL of toluene were put into a 250 mL Schlenk flask.

Palladium acetate (Pd(OAc)$_2$) (OAc=acetate, 1.7 mg, and 2.48 μmol) and tricyclohexylphosphonium(tetrakis pentafluorophenyl)borate ([(Cy)$_3$PH][B(C$_6$F$_5$)$_4$]) (4.8 mg and 4.96 μmol) were used and the polymerization was performed by using the same procedure as Example 39 to recover the polymer. 1.88 g of 5-norbornene-2-methyl acetate polymer (91 wt % on the basis of the total amount of the added monomers) was obtained by using the polymerization.

The weight average molecular weight (Mw) of the polymer was 639,000, and Mw/Mn was 3.79.

Example 13

Copolymerization of 5-norbornene-2-methyl acetate where exo/endo=90/10

5-norbornene-2-methyl acetate (NB—$CH_2$—O—C(C)—$CH_3$) where exo/endo=90/10 (2.06 g, 12.4 mmol, and NB denotes norbornene) and 6 mL of toluene were put into a 250 mL Schlenk flask. Palladium acetate (Pd(OAc)$_2$) (OAc=acetate, 1.7 mg, and 2.48 mol) and tricyclohexylphosphonium(tetrakis pentafluorophenyl)borate ([(Cy)$_3$PH][B(C$_6$F$_5$)$_4$]) (4.8 mg and 4.96 mmol) were used and the polymerization was performed by using the same procedure as Example 39 to recover the polymer. 2.04 g of 5-norbornene-2-methyl acetate polymer (>99 wt % on the basis of the total amount of the added monomers) was obtained by using the polymerization.

The weight average molecular weight (Mw) of the polymer was 764,000, and Mw/Mn was 4.58.

Example 14

Copolymerization of 5-norbornene-2-methyl acetate where exo/endo=70/30 and 5-norbornene-2-acetate where exo/endo=100/0

5-norbornene-2-methyl acetate (NB—$CH_2$—O—C(O)—$CH_3$) where exo/endo=70/30 (1.76 g and 10.6 mmol), 5-norbornene-2-acetate (NB—O—C(O)—$CH_3$) where exo/endo=100/0 (0.40 g and 2.6 mmol), and 10 mL of toluene were put into a 250 ml. Schlenk flask.

1 mL of dichloromethane was added to palladium acetate (Pd(OAc)$_2$) (OAc=acetate, 1.8 mg, and 2.6 μmol) and tricyclohexylphosphonium(tetrakis pentafluorophenyl)borate ([(Cy)$_3$PH][B(C$_6$F$_5$)$_4$]) (5.1 mg and 5.3 μmol) to perform dissolution and the resulting solution was added to the monomer solution. The reaction temperature was increased to 90° C. and agitation was performed for 3 hours. After the reaction for 3 hours, the polymer was recovered by using the same procedure as Example 39. Thereby, 1.75 g of 5-norbornene-2-methyl acetate/5-norbornene-2-acetate copolymer was obtained (81 wt % on the basis of the total amount of the added monomers).

The weight average molecular weight (Mw) of the polymer was 342,900, and Mw/Mn was 2.89.

Example 15

Copolymerization of 5-norbornene-2-methyl acetate where exo/endo=54/46 and butylnorbornene 5-norbornene-2-methyl acetate where exo/endo=54/46 (NB—$CH_2$—O—C(O)—$CH_3$) (14.54 g and 0.0875 mol), butylnorbornene (5.59 g and 0.0375 μmol), and toluene (40.26 g) were put into a 250 mL Schlenk flask.

1 mL of dichloromethane was added to palladium acetate (Pd(OAc)$_2$) (OAc=acetate, 1.9 mg, and 8 μmol) and tricyclohexylphosphonium(tetrakis pentafluorophenyl)borate ([(Cy)$_3$PH][B(C$_6$F$_5$)$_4$]) (16 mg and 17 μmol) to perform dissolution and the resulting solution was added to the monomer solution. The reaction temperature was increased to 90° C. and agitation was performed for 18 hours.

After the reaction for 18 hours, 67.1 g of toluene was added to dilute the polymer solution having the high viscosity, and the diluted polymer solution was added to an excessive amount of ethanol to obtain a white copolymer precipitate. The precipitate was filtered by using a glass funnel and the recovered copolymer was dried in a vacuum oven at 70° C. for 24 hours to obtain 19.12 g of 5-norbornene-2-methyl acetate/butylnorbornene copolymer (95 wt % on the basis of the total amount of the added monomers).

The weight average molecular weight (Mw) of the polymer was 303,550, and Mw/Mn was 2.16.

Example 16

Copolymerization of 5-norbornene-2-methyl acetate where exo/endo=70/30 and hexylnorbornene 5-norbornene-2-methyl acetate where exo/endo=70/30 (NB—$CH_2$—O—C(O)—$CH_3$) (1.10 g and 6.60 mmol), hexylnorbornene (1.17 g and 6.60 mmol), and 6 mL of toluene were put into a 250 mL Schlenk flask.

Palladium acetate (Pd(OAc)$_2$) (OAc=acetate, 1.8 mg, and 2.6 mol) and tricyclohexylphosphonium(tetrakis pentafluorophenyl)borate ([(Cy)$_3$PH][B(C$_6$F$_5$)$_4$]) (5.1 mg and 5.3 mol) were used and the polymerization was performed by using the same procedure as Example 39 to recover the polymer. 2.17 g of 5-norbornene-2-methyl acetate/hexylnorbornene copolymer (96 wt % on the basis of the total amount of the added monomers) was obtained by using the polymerization.

The weight average molecular weight (Mw) of the polymer was 555,500, and Mw/Mn was 3.76.

Example 17

Copolymerization of 5-norbornene-2-methyl acetate wherein exo/endo=54/46 and 5-norbornene-2-carboxylic acid methyl estel 5-norbornene-2-methyl acetate wherein exo/endo=54/46 (14.54 g and 0.0875 mol), 5-norbornene-2-carboxylic acid methyl ester (5.71 g and (0.0375 mol), and toluene (30.37 g) were put into a 250 mL Schlenk flask.

1 mL of dichloromethane was added to palladium acetate (Pd(OAc)$_2$) (OAc=acetate, 1.9 mg, and 8 μmol) and tricyclohexylphosphonium(tetrakis pentafluorophenyl)borate ([(Cy)$_3$PH][B(C$_6$F$_5$)$_4$]) (16 mg and 17 μmol) to perform dissolution and the resulting solution was added to the monomer solution.

The reaction temperature was increased to 90° C. and agitation was performed for 18 hours. After the reaction for 18 hours, 50.61 g of toluene was added to dilute the polymer solution having the high viscosity, and the diluted polymer solution was added to an excessive amount of ethanol to obtain a white copolymer precipitate.

The precipitate was filtered by using a glass funnel and the recovered copolymer was dried in a vacuum oven at 70° C. for 24 hours to obtain 18.32 g of copolymer of 5-norbornene-2-methyl acetate and 5-norbornene-2-carboxylic acid methyl ester (90.5 wt % on the basis of the total amount of the added monomers).

The weight average molecular weight (Mw) of the polymer was 211,891, and Mw/Mn was 2.67.

Example 18

Terpolymerization of 5-norbornene-2-methyl acetate where exo/endo=70/30,5-norbornene-2-acetate where exo/endo=100/0, and hexylnorbornene 5-norbornene-2-methyl acetate where exo/endo=70/30 (NB—$CH_2$—O—C(O)—$CH_3$) (1.76 g and 10.6 mmol), 5-norbornene-2-acetate where exo/endo=100/0 (NB—O—C(O)—$CH_3$) (0.20 g and 1.30 mmol), hexylnorbornene (0.23 g and 1.30 mmol), and 10 ml of toluene were put into a 250 mL Schlenk flask. 1 mL of dichloromethane was added to palladium acetate (Pd(OAc)$_2$) (OAc=acetate, 1.8 mg, and 2.6 μmol) and tricyclohexylphosphonium(tetrakis pentafluorophenyl) borate ([(Cy)$_3$PH][B(C$_6$F$_5$)$_4$]) (5.1 mg and 5.3 μmol) to perform dissolution and the resulting solution was added to the monomer solution.

The reaction temperature was increased to 90° C. and agitation was performed for 3 hours. After the reaction for 3 hours, the polymer was recovered by using the same procedure as Example 39. Thereby, 1.89 g of 5-norbornene-2-methyl acetate/5-norbornene-2-acetate/hexylnorbornene copolymer was obtained (86 wt % on the basis of the total amount of the added monomers).

The weight average molecular weight (Mw) of the polymer was 419,900, and Mw/Mn was 2.60.

Example 19

Terpolymerization of 5-norbornene-2-methyl acetate where exo/endo=54/46, butylnorbornene, and hexylnorbornene 5-norbornene-2-methyl acetate where exo/endo=54/46 (NB—$CH_2$—O—C(O)—$CH_3$) (1.10 g and 6.60 mmol), butylnorbornene (0.50 g and 3.30 mol), hexylnorbornene (0.58 g and 3.30 mol), and 6 ml of toluene were put into a 250 mL Schlenk flask.

Palladium acetate (Pd(OAc)$_2$) (OAc=acetate, 1.8 mg, and 2.6 μmol) and tricyclohexylphosphonium(tetrakis pentafluorophenyl)borate ([(Cy)$_3$PH][B(C$_6$F$_5$)$_4$]) (5.1 mg and 5.3 μmol) were used and the polymerization was performed by using the same procedure as Example 39 to recover the polymer. 2.05 g of 5-norbornene-2-methyl acetate/butylnorbornene/hexylnorbornene copolymer (94 wt % on the basis of the total amount of the added monomers) was obtained by using the polymerization.

The weight average molecular weight (Mw) of the polymer was 510,200, and Mw/Mn was 3.63.

Examples 20 TO 29

Production of an Optical Film

The norbornene polymers that were produced in Examples 10 to 19 were mixed so that the compositions of Table 2 were obtained to produce coating solutions, and the coating solutions were cast on a glass substrate by using a knife coater or a barcoater, dried at normal temperature for 1 hour, and additionally dried in a nitrogen atmosphere at 100° C. for 18 hours.

After the drying, the dried substrate was stored at −10° C. for 10 sec, and the film was peeled off from the glass substrate by using a knife to obtain a transparent film having a uniform thickness where a thickness deviation is less than 2%. The thickness and light transmission at 400 to 800 nm of the film are described in the following Table 2.

(Measurement of Optical Anisotropic Properties)

In respects to the transparent films, the refractive index (n) was measured by using an ABBE refractometer, the in-plane retardation value ($R_e$) was measured by using an automatic birefringence analyzer (KOBRA-21 ADH manufactured by Oji scientific instrument, Co., Ltd.), the retardation value ($R_\theta$) was measured in the case where incident light meets the film surface at the angle of 50°, and the retardation value ($R_{th}$) in respects to the direction through the film thickness and the in-plane x-axis was obtained by using the following Equation 2.

$$R_{th} = \frac{R_\theta \times \cos\theta_f}{\sin^2\theta_f} \quad \text{(Equation 2)}$$

wherein θ is an incident angle and $\theta_f$ is a refraction angle of a film.

In addition, the $R_e$ and $R_{th}$ values were divided by the thickness of the film to obtain a difference in refractive index $(n_x-n_y)$ and a difference in refractive index $(n_y-n_z)$. $(n_x-n_y)$, $R_\theta$, $R_{th}$, and $(n_y-n_z)$ of the transparent film are described in the following Table 2.

temperature of 230 to 330° C. for a reaction time of 5 min to 24 hours so that a content of an exo isomer is 50 mol % or more:

$$CH_2=CH-(CH_2)_n-OC(O)R \quad \text{<Formula 1>}$$

wherein n is an integer of 0 to 10, and R is an alkyl group having 1 to 20 carbon atoms.

2. The method for producing the norbornene monomer composition according to claim 1, wherein a molar ratio of the compound represented by Formula 1 to cyclopentadiene, dicyclopentadiene, or the mixture of cyclopentadiene and dicyclopentadiene in the reaction solution is in the range of 1:1 to 1:10.

3. The method for producing the norbornene monomer composition according to claim 1, wherein the compound represented by Formula 1 is allyl acetate.

TABLE 2

| | Composition of the film solution | | Physical properties of the film | | | | | |
|---|---|---|---|---|---|---|---|---|
| Example | Polymer (part by weight) | Solvent (part by weight) | Thickness (μm) | Light transmission (%) | n Refractive index | $(n_x - n_y) \times 10^3$ | $R_{th}$ (nm/μm) | $(n_y - n_z) \times 10^3$ |
| 20 | Polymer 100 of Example 10 | Toluene 560 | 95 | 92 | 1.53 | 0.015 | 4.72 | 4.72 |
| 21 | Polymer 100 of Example 11 | MC 360/ Toluene 200 | 102 | 91 | 1.52 | 0.011 | 4.43 | 4.43 |
| 22 | Polymer 100 of Example 12 | MC 360/ Toluene 200 | 103 | 91 | 1.52 | 0.009 | 4.38 | 4.38 |
| 23 | Polymer 100 of Example 13 | MC 360/ Toluene 200 | 88 | 92 | 1.52 | 0.010 | 4.33 | 4.33 |
| 24 | Polymer 100 of Example 14 | MC 360/ Toluene 200 | 105 | 91 | 1.52 | 0.014 | 4.52 | 4.52 |
| 25 | Polymer 100 of Example 15 | Toluene 560 | 120 | 90 | 1.51 | 0.010 | 3.53 | 3.53 |
| 26 | Polymer 100 of Example 16 | Toluene 560 | 99 | 90 | 1.50 | 0.009 | 3.06 | 3.06 |
| 27 | Polymer 100 of Example 17 | MC 360/ Toluene 200 | 102 | 91 | 1.53 | 0.007 | 4.66 | 4.66 |
| 28 | Polymer 100 of Example 18 | MC 360/ Toluene 200 | 108 | 91 | 1.51 | 0.011 | 4.10 | 4.10 |
| 29 | Polymer 100 of Example 19 | MC 360/ Toluene 200 | 94 | 90 | 1.50 | 0.005 | 3.11 | 3.11 |

In Table 2, MC denotes methylene chloride.

Furthermore, in the case where the triacetate cellulose film where $n_y>n_z$ was provided to measure $R_\theta$, the $R_\theta$ values of all the films were increased. This means that $R_{th}$ of the film is caused by the negative birefringence $(n_y>n_z)$ in the thickness direction.

INDUSTRIAL APPLICABILITY

According to the present invention, in order to produce an acetate norbornene monomer composition containing an exo isomer in content of 50 mol % or more, variables such as a reaction temperature, a reaction time, a molar ratio between reactants, and addition of a solvent are controlled. Thus, it is possible to industrially produce the acetate norbornene monomer composition, a norbornene polymer produced using the composition, and an optical film including the polymer using an easy process.

The invention claimed is:

1. A method for producing a norbornene monomer composition, comprising:
the step of reacting a reaction solution that comprises cyclopentadiene, dicyclopentadiene, or a mixture of cyclopentadiene and dicyclopentadiene; a compound represented by Formula 1; and a solvent; at a reaction

4. The method for producing the norbornene monomer composition according to claim 1, wherein the reaction solution further comprises at least one polymerization inhibitor selected from the group consisting of aniline, cyclohexane, phenol, 4-ethoxyphenol, nitrobenzene, hydroquinone, benzoquinone, copper dichloride, and 2,2-di(4-tert-octylphenyl)-1-picrylhydrazyl.

5. The method for producing the norbornene monomer composition according to claim 4, wherein the polymerization inhibitor is contained in an amount of 0.01 to 100 parts by weight based on 100 parts by weight of cyclopentadiene, dicyclopentadiene, or the mixture of cyclopentadiene and dicyclopentadiene, and the compound represented by Formula 1.

6. The method for producing the norbornene monomer composition according to claim 1, wherein the solvent contains at least one selected from the group consisting of cyclohexane, toluene, acetone, methyl ethyl ketone (MEK), ethyl acetate, dimethyl sulfoxide (DMSO), tetrahydrofuran (THF), and dimethyl formamide (DMF).

7. The method for producing the norbornene monomer composition according to claim 1, wherein the method is performed so that a reaction quotient represented by Equation 1 is in the range of 25,200 to 350,000:

Reaction quotient=reaction temperature (° C.)$^2$×log (reaction time (min)).  <Equation 1>

8. A method for producing a norbornene polymer comprising:
preparing a norbornene monomer composition in accordance with the method of claim 1,
bringing a reactant that contains the norbornene monomer composition having an exo isomer in a content of 50 mol % or more into contact with a catalyst of a transition metal of Group 10:

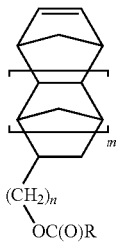

[Formula 5]

wherein m is an integer in the range of 0 to 4, n is an integer in the range of 0 to 10, and R is an alkyl group having 1 to 20 carbon atoms, and
wherein the monomer composition contains at least two types of monomers selected from compounds represented by Formula 5.

9. The method for producing a norbornene polymer according to claim 8, wherein the reactant further contains a polar norbornene monomer represented by Formula 6:

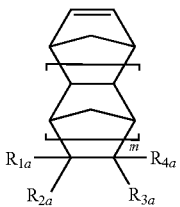

<Formula 6> wherein m is an integer of 0 to 4,
at least one of $R_{1a}$, $R_{2a}$, $R_{3a}$, and $R_{4a}$ is a polar functional group containing at least one atom selected from the group consisting of oxygen, nitrogen, phosphorus, sulfur, silicon, and boron, and
$R_{1a}$, $R_{2a}$, $R_{3a}$, and $R_{4a}$ that are not the polar functional group are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1a}$ and $R_{2a}$ or $R_{3a}$ and $R_{4a}$ and has 1 to 10 carbon atoms; a saturated or unsaturated cyclic group that is formed by bonding of $R_{1a}$ or $R_{2a}$ to either of $R_{3a}$ and $R_{4a}$ and has 4 to 12 carbon atoms; or an aromatic cyclic compound that has 6 to 24 carbon atoms.

10. The method for producing a norbornene polymer according to claim 8, herein the reactant further contains a nonpolar norbornene monomer represented by Formula 7:

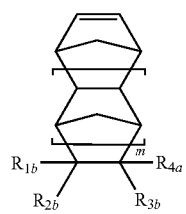

<Formula 7> wherein m is an integer of 0 to 4, and
$R_{1b}$, $R_{2b}$, $R_{3b}$, and $R_{4b}$ are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1b}$ and $R_{2b}$ or $R_{3b}$ and $R_{4b}$ and has 1 to 10 carbon atoms; a saturated or unsaturated cyclic group that is formed by bonding of $R_{1b}$ or $R_{2b}$ to either of $R_{3b}$ and $R_{4b}$ and has 4 to 12 carbon atoms; or an aromatic cyclic compound that has 6 to 24 carbon atoms.

11. The method for producing a norbornene polymer according to claim 8, wherein the reactant further contains a polar norbornene monomer represented by Formula 6 and a nonpolar norbornene monomer represented by Formula 7:

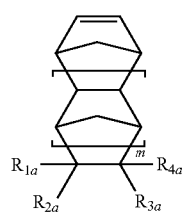

<Formula 6>

<Formula 7>

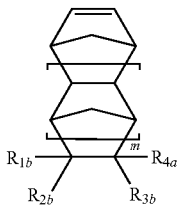

wherein each m is independently an integer of 0 to 4, at least one of $R_{1a}$, $R_{2a}$, $R_{3a}$, and $R_{4a}$ is a polar functional group containing at least one atom selected from the group consisting of oxygen, nitrogen, phosphorus, sulfur, silicon, and boron, and $R_{1a}$, $R_{2a}$, $R_{3a}$, and $R_{4a}$ that are not the polar functional group are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1a}$ and $R_{2a}$ or $R_{3a}$ and $R_{4a}$ and has 1 to 10 carbon atoms; a saturated or unsaturated cyclic group that is formed by bonding of $R_{1a}$ or $R_{2a}$ to either of $R_{3a}$ and $R_{4a}$ and has 4 to 12 carbon atoms; or an aromatic cyclic compound that has 6 to 24 carbon atoms, and $R_{1b}$, $R_{2b}$, $R_{3b}$, and $R_{4b}$ are each independently hydrogen; halogen; linear or branched alkyl, alkenyl, or vinyl having 1 to 20 carbon atoms; cycloalkyl that is substituted or unsubstituted with hydrocarbon and has 5 to 12 carbon atoms; aryl that is substituted or unsubstituted with hydrocarbon and has 6 to 40 carbon atoms; aralkyl that is substituted or unsubstituted with hydrocarbon and has 7 to 15 carbon atoms; alkynyl that has 3 to 20 carbon atoms; linear or branched haloalkyl, haloalkenyl, or halovinyl that has 1 to 20 carbon atoms; halocycloalkyl that is substituted or unsubstituted with hydrocarbon and has 5 to 12 carbon atoms; haloaryl that is substituted or unsubstituted with hydrocarbon and has 6 to 40 carbon atoms; haloaralkyl that is substituted or unsubstituted with hydrocarbon and has 7 to 15 carbon atoms; haloalkynyl that has 3 to 20 carbon atoms; an alkylidene group that is formed by bonding of $R_{1b}$ and $R_{2b}$ or $R_{3b}$ and $R_{4b}$ and has 1 to 10 carbon atoms; a saturated or unsaturated cyclic group that is formed by bonding of $R_{1b}$ or $R_{2b}$ to either of $R_{3b}$ and $R_{4b}$ and has 4 to 12 carbon atoms; or an aromatic cyclic compound that has 6 to 24 carbon atoms.

* * * * *